(12) United States Patent
Karlou-Eyrisch et al.

(10) Patent No.: US 6,590,094 B2
(45) Date of Patent: Jul. 8, 2003

(54) SUPERPARAMAGNETIC BEAD POLYMERS

(75) Inventors: Kamelia Karlou-Eyrisch, Düsseldorf (DE); Wolfgang Podszun, Köln (DE); Rainer Neumann, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/903,006

(22) Filed: Jul. 11, 2001

(65) Prior Publication Data

US 2002/0106659 A1 Aug. 8, 2002

(30) Foreign Application Priority Data

Jul. 11, 2000 (DE) .......................... 100 33 583

(51) Int. Cl.[7] .................. C07H 21/00; C07H 21/04; C12Q 1/68; C12P 19/34; C12M 1/34
(52) U.S. Cl. .................. 536/25.4; 436/6; 436/7.1; 436/91.1; 436/91.2; 436/287.2; 536/22.1; 536/23.1; 536/24.3; 536/24.31; 536/24.32; 536/24.33; 526/80
(58) Field of Search ................ 435/6, 7.1, 91.1, 435/91.2, 287.6; 536/22.1, 23.1, 24.3–33, 25.4; 526/80

(56) References Cited

U.S. PATENT DOCUMENTS

| 4,339,337 A | 7/1982 | Tricot et al. ............. 252/62.54 |
| 5,206,159 A | 4/1993 | Cohen et al. ................ 435/180 |
| 5,356,713 A | 10/1994 | Charmot et al. ............ 428/407 |
| 5,705,628 A | 1/1998 | Hawkins .................... 536/25.4 |

FOREIGN PATENT DOCUMENTS

| DE | 4333805 | 2/1995 |
| EP | 0707077 | 4/1996 |
| WO | 8303920 | 10/1983 |

*Primary Examiner*—Jeffrey Siew
(74) *Attorney, Agent, or Firm*—Jeffrey M. Greenman; Andrew L. Klawitter

(57) ABSTRACT

The invention relates to crosslinked bead polymers doped with superparamagnetic iron oxide, to a process for the preparation of the bead polymers, and to the use thereof in nucleic acid diagnosis.

6 Claims, No Drawings

SUPERPARAMAGNETIC BEAD POLYMERS

The invention relates to crosslinked bead polymers doped with superparamagnetic iron oxide, to a process for the preparation of the bead polymers, and to the use thereof in nucleic acid diagnosis.

So-called genetic diagnosis has become increasingly important recently.

Genetic diagnosis has become involved in the diagnosis of human diseases (inter alia detection of pathogens, detection of genome mutations, discovery of circulating tumour cells and identification of risk factors for predisposition to a disease). However, genetic diagnosis is also now finding applications in veterinary medicine, environmental analysis and food testing. A further area of application comprises investigations in institutes of pathology/cytology or within the framework of forensic problems. However, genetic diagnosis is now employed also for the purposes of quality control (for example investigations of blood samples for freedom from pathogens), and legislation is planned to regulate such tests by law in future. Methods also employed in genetic diagnosis (such as, for example, hybridization and amplification techniques such as PCR, bDNA or NASBA technology) are also among the routine methods in fundamental scientific studies.

An important step in genetic diagnosis is the obtaining of gene samples from biological material such as cells, blood, serum or urine.

EP 0 707 077 describes a method for isolating nucleic acids from biological material using soluble, weakly basic polymer. In this method, a precipitation product is generated from the soluble, weakly basic polymer and the nucleic acid in an acidic pH range, the precipitation product is separated from the unprecipitated constituents of the biological material, and washed, and the nucleic acid is liberated again from the precipitation product by adjusting a basic pH.

One disadvantage of the method in EP 0 707 077 is that the manipulation, in particular the separation and purification of the precipitation product, is difficult and very time consuming. This method can moreover be carried out using automatic analysers only under difficult conditions or not at all.

U.S. Pat. No. 4,339,337 and U.S. Pat. No. 5,356,713 describe methods for preparing magnetic beads of vinylaromatic polymer using magnetic particles. These bead polymers do not, however, contain any functional groups for attaching nucleic acids. In addition, the beads show a marked residual magnetism (remanence), which impedes dispersability thereof.

WO 8303920 describes a method for preparing magnetic polymer particles in which polymer particles are treated with solutions of, for example, iron salt, the iron being precipitated in the form of iron hydroxide. In this method, the precipitated iron compound is present both in the polymer particles and on the surface of the polymer particles. The iron compound on the surface may interfere with some applications, for example amplification of nucleic acids by Taqman PCR.

U.S. Pat. No. 5,206,159 discloses a process for preparing superparamagnetic polyacrylamide carriers. These carriers are, however, unsuitable for removing nucleic acids.

U.S. Pat. No. 5,705,628 discloses a method for binding DNA to magnetic microparticles. The magnetic microparticles preferably have a particle size of 1 $\mu$m and have a surface coated with carboxyl groups. In order to achieve binding of the DNA to the particles it is necessary to use a specific salt concentration and add polyethylene glycol in a defined concentration and with specific molecular weight.

It has now been found that certain crosslinked bead polymers doped with superparamagnetic iron oxide and containing basic amino groups are outstandingly suitable for direct and automated isolation of nucleic acids.

The invention relates to crosslinked bead polymers doped with superparamagnetic iron oxide and containing basic amino groups, which are characterized in that the bead polymers contain copolymerized units of hydrophilic (meth) acrylate and amino (meth)acrylates.

The term (meth)acrylate means the derivatives of acrylic acid and methacrylic acid.

Hydrophilic (meth)acrylates are those whose homopolymers have a solubility of more than 2.5% in water at 25° C. Examples which may be mentioned are: 2-hydroxyethyl methacrylate, 2-hydroxypropyl methacrylate, 2-hydroxyethyl acrylate, 2-hydroxypropyl acrylate, triethylene glycol monomethacrylate, tetraethylene glycol monomethacrylate, glycerol monomethacrylate, acrylamide, methacrylamide and N,N-dimethylacrylamide. Acrylamide is preferred.

Amino (meth)acrylates for the purpose of the present invention are derivatives of acrylic acid and methacrylic acid with, preferably, secondary and tertiary amino groups. The amino groups may also be part of a cycloaliphatic or aromatic ring. Suitable amino (meth)acrylates are, for example, N-(3-aminopropyl)methacrylamide, N-(3-imidazolylpropyl)methacrylamide, N-(2-imidazolylethyl) methacrylamide, N-(3-aminopropyl)acrylamide, N-(3-imidazolylpropyl)acrylamide, N-(2-imidazolylethyl) acrylamide, N-(1,1-dimethyl-3-imidazolylpropyl) methacrylamide, N-(1,1-dimethyl-3-imidazoylpropyl) acrylamide, N-(3-benzimidazolylpropyl)-methacrylamide and (3-benzimidazolylpropyl)acrylamide. Preferred amino (meth)acrylates are aminoalkyl (meth)acrylates such as, for example, N,N-dimethylaminoethyl methacrylate, N,N-dimethylaminopropyl methacrylate, N,N-dimethylaminoethyl acrylate, and N-tert-butylaminopropyl methacrylate. N,N-Dimethylaminoethyl methacrylate and N,N-dimethylaminopropyl methacrylate are particularly preferred. The amino groups in the bead polymers according to the invention may be wholly or partly in protonated form, for example as hydrochlorides.

Suitable crosslinkers are: ethylene glycol dimethacrylate, butanediol dimethacrylate, hexanediol dimethacrylate, pentaerythritol dimethacrylate, glycerol 1,2-dimethacrylate, glycerol 1,3-dimethacrylate, triethylene glycol dimethacrylate, tetraethylene glycol dimethacrylate, trimethylolpropane trimethacrylate, pentaerythritol trimethacrylate, pentaerythritol tetramethacrylate, ethylene glycol diacrylate, butanediol diacrylate, pentaerythritol diacrylate, glycerol 1,3-diacrylate, triethylene glycol diacrylate, trimethylolpropane triacrylate, pentaerythritol triacrylate, pentaerythritol tetraacrylate, allyl methacrylate, allyl acrylate, diethylene glycol divinyl ether and methylene-N,N'-bisacrylamide. Methylene-N,N'-bisacrylamide is preferred.

The amount of hydrophilic (meth)acrylate is 30 to 89% by weight, preferably 40 to 75% by weight, the amount of amino (meth)acrylates is 10 to 69% by weight, preferably 20 to 50% by weight, and the amount of crosslinker is 1 to 25% by weight, in each case based on the total of hydrophilic (meth)acrylate, amino (meth)acrylates and crosslinker.

The content of iron oxide in the superparamagnetic bead polymers according to the invention is 2 to 80% by weight, preferably 4 to 50% by weight, particularly preferably 5 to 35% by weight, based on the weight of the unswollen bead polymers.

The bead polymers according to the invention are superparamagnetic, that is to say they have a low residual magnetization (remanence) and a small coercivity. Their magnetic saturation is high, and they are strongly attracted by an inhomogeneous magnetic field. After the magnetic field has been switched off, they can be dispersed easily and completely in water or aqueous buffer solutions.

The particle size of these superparamagnetic bead polymers according to the invention is 1 to 200 μm, preferably 5 to 100, particularly preferably 10 to 50 μm. Microscopic image analysis is very suitable for determining the average particle size (Ø) and the particle size distribution.

As a measure of the breadth of the particle size distribution of the bead polymers, the ratio is formed from the average of the volume distribution ($D_v$) and the average of the number distribution ($D_z$). Narrow particle size distributions for the purpose of the invention mean $D_v/D_z \leq 2.5$, preferably $D_v/D_z \leq 2$, particularly preferably $D_v/D_z \leq 1.5$. It has been found that bead polymers according to the invention with a narrow particle size distribution are particularly suitable for isolating nucleic acids and provide results with particularly good reproducibility in amplification methods on the surface of the bead polymers.

The bead polymers according to the invention are swellable in water. They have a swelling index of 1.25 to 8, preferably 2 to 6 (measured at 25° C.). The swelling index is defined as the quotient of the volume of the swollen bead polymer and the volume of the unswollen bead polymer.

For experimental determination of the swelling index, 10 ml of dried, screened bead polymer are weighed into a 100 ml graduated cylinder. The quotient of the volume of the bed ($V_0$) and the weighed amount (m) is the bulk volume ($V_{bulk}$). The graduated cylinder is made up to 100 ml with water and left to stand at 25° C. for 10 to 20 h. During this, it is shaken occasionally and it is ensured that any air bubbles appearing can escape. The volume of the swollen bed is read off and gives $V_1$. The quotient of $V_1$ and $V_0$ is the swelling index.

The present invention further relates to a process for preparing crosslinked bead polymers, which is characterized in that a monomer mixture of hydrophilic (meth)acrylate, amino (meth)acrylate, crosslinker and, where appropriate, other monomer is polymerized to beads by inverse suspension polymerization, and the latter are then doped with superparamagnetic iron oxide by an after-treatment with iron salt solution.

Inverse suspension polymerization means for the purpose of the invention a process in which the monomer mixture of hydrophilic (meth)acrylate, amino (meth)acrylate, crosslinker and, where appropriate, other monomer is activated with a free-radical former which is soluble in the monomer mixture, and the activated monomer mixture is emulsified with addition of a dispersing aid in a nonaqueous solvent to give droplets, and then the droplets which have formed are cured by raising the temperature.

The hydrophilic (meth)acrylate, the amino (meth)acrylate and the crosslinker correspond to the compounds mentioned above. The amino (meth)acrylate can moreover advantageously be employed at least partly in the ammonium form, for example as hydrochloride. Suitable as other monomer are, for example, N-vinylpyrrolidone, vinylimidazole, styrene, alpha-methylstyrene, chloromethylstyrene, acrylonitrile, vinyl acetate and maleic anhydride, in amounts of up to about 25% by weight based on the complete mixture of monomers. It is beneficial to dilute the monomer mixture with water or water/alcohol mixtures. Suitable amounts of diluent are, for example, 10 to 200% by weight, preferably 50 to 150% by weight, based on the monomer mixture.

Suitable free-radical formers are azo compounds and peroxy compounds. When water is used as diluent, potassium peroxodisulphate and sodium peroxodisulphate are very suitable, also in combination with bisulphite or hydrogen sulphite. Other preferred free-radical formers are the azo compounds such as 2,2'-azobis[2-(2-imidazolin-2-yl) propane] dihydrochloride and 2,2'-azobis(2-amidinopropane) dihydrochloride. The free-radical former is used in amounts of 0.02 to 2.5% by weight, preferably of 0.1 to 1% by weight, based on the complete mixture of monomers.

Suitable as nonaqueous solvents for the purpose of the present invention are primarily hydrocarbons and halogenated hydrocarbons, and low-viscosity silicone oils. Preference is given to linear, branched and cyclic aliphatic hydrocarbons. Examples which may be mentioned are hexane, heptane, n-octane, isooctane, isododecane and cyclohexane. It is, of course, also possible to use mixtures of different hydrocarbons.

Suitable dispersing aids are oil-soluble polymers with a molecular weight of 2 000 to 1 000 000. Preference is given to polymers containing copolymerized units of $C_6$- to $C_{22}$-alkyl (meth)acrylates and/or vinyl ester of $C_6$- to $C_{22}$-carboxylic acids. Examples which may be mentioned are polymers with copolymerized units of stearyl methacrylate, lauryl methacrylate and vinyl stearate. Copolymers of $C_6$- to $C_{22}$-alkyl (meth)acrylates and vinyl ester of $C_6$- to $C_{22}$-carboxylic acids and hydrophilic monomers are particularly suitable. Hydrophilic monomers mean in this connection polymerizable olefinically unsaturated compounds which are wholly or partly (more than 2.5% by weight at 20° C.) soluble in water. Examples which may be mentioned are: acrylic acid and its alkali metal and ammonium salts, methacrylic acid and its alkali metal and ammonium salts, hydroxyethyl methacrylate, hydroxyethyl acrylate, diethylene glycol monoacrylate, diethylene glycol monomethacrylate, triethylene glycol monoacrylate, triethylene glycol monomethacrylate, tetraethylene glycol monoacrylate, tetraethylene glycol monomethacrylate, glycerol monoacrylate, aminoethyl methacrylate, N,N-dimethylaminoethyl methacrylate, acrylamide, methacrylamide, vinylpyrrolidone and vinylimidazole. Preference is given to hydroxyethyl methacrylate, aminoethyl methacrylate, N,N-dimethylaminoethyl methacrylate, acrylamide, methacrylamide, vinylpyrrolidone and vinylimidazole.

Particularly preferred dispersing aids are copolymers of

---

75 to 99% by weight of $C_6$- to $C_{22}$-alkyl (meth)acrylate
and/or vinyl ester of $C_6$- to $C_{22}$carboxylic acids and
1 to 25% by weight of hydrophilic monomer from the group of
hydroxyethyl methacrylate, aminoethyl methacrylate,
N,N-dimethylaminoethyl methacrylate, acrylamide, methacrylamide,
vinylpyrrolidone and vinylimidazole.

---

The amount of the dispersing aid employed is generally 0.1 to 8, preferably 0.5 to 5, % by weight, based on the nonaqueous solvent.

The stirring speed during the polymerization is important for adjusting the particle size. In the process according to the invention, the size of the bead polymers obtained decreases as the stirrer speed increases. The exact stirrer speed to adjust to a particular predetermined bead size depends in the individual case greatly on the size of the reactor, the geometry of the reactor and the geometry of the stirrer. It has proved to be expedient to find the stirrer speed necessary by experiment. For laboratory reactors with a reaction volume of 0.51 and equipped with a gate stirrer, in general bead diameters of 10 to 25 µm are obtained on use of copolymers of methacrylic acid $C_{13}$-ester and hydroxyethyl methacrylate as dispersing aid with speeds of 800 to 1 000 rpm.

The polymerization temperature depends on the decomposition temperature of the initiator employed and on the boiling point of the nonaqueous solvent. It is generally between 50 and 150° C., preferably between 55 and 100° C. The polymerization takes 0.5 to some hours (for example 10 hours).

After the polymerization it is possible for the polymer to be isolated by conventional methods, for example by filtration or decantation, and, where appropriate after one or more washing steps, be dried. It is possible to fractionate the resulting bead polymer by physical methods in order to adjust to a narrower particle size distribution. Suitable fractionation methods are, for example, screening, sedimentation and air classification.

The after-treatment for doping with superparamagnetic iron oxide takes place with mixtures of aqueous $Fe^{2+}$ and $Fe^{3+}$ salt solutions. The corresponding chlorides are very suitable. The $Fe^{2+}:Fe^{3+}$ molar ratio should in this case be 2:1 to 1:2. It is moreover possible to start from iron salt solutions with a different $Fe^{2+}:Fe^{3+}$ ratio and to effect the optimal $Fe^{2+}:Fe^{3+}$ ratio by using oxidizing or reducing agents. Examples of oxidizing agents are peroxo and nitro compounds, and an example of a suitable reducing agent is sodium bisulphite. The concentration of the iron salt solutions is generally 10 to 50% by weight, preferably 20 to 40% by weight.

The iron salt solution is preferably brought into contact with dry, anhydrous bead polymer. It is particularly advantageous in this connection if the bead polymer swells by taking up the entire iron salt solution; and no excess iron salt solution remains in the interstices of the beads or on the surface of the beads.

The iron salts taken up by the swollen bead polymer are converted into the corresponding iron hydroxides by adding bases. Alkaline solutions of sodium hydroxide, sodium carbonate or ammonia are very suitable. Ammonia is preferred because an excess can easily be removed by evaporation. Ammonium salts formed are removed by thorough washing with water.

The iron hydroxide is converted into iron oxide (dehydrated) by heating the bead polymer. The heat treatment in this case can take place in a simple manner in aqueous suspension at 65 to 100° C. Suitable heating times are 0.5 to 5 hours. The conversion of the iron hydroxide into iron oxide is evident from the change in colour from pale brown to dark brown or black. The bead polymer is then removed and dried.

If required, the dried bead polymers doped with superparamagnetic iron oxide obtained in this way can be treated once more in the manner described above, in which case the content of superparamagnetic iron oxide is increased. It is possible in this way to set iron oxide contents of more than 50% by weight.

The present invention further relates to a process for isolating nucleic acids from a sample, comprising the following steps A) mixing the sample with a bead polymer at a pH of 7 or below, the nucleic acids being adsorbed,
B) removing the bead polymer including the adsorbed nucleic acids using a magnetic field and
C) mixing the bead polymer with an aqueous phase with a pH above 7, the adsorbed nucleic acids being released, which is characterized in that the bead polymer is doped with superparamagnetic iron oxide, and contains copolymerized units of hydrophilic (meth)acrylate and amino (meth)acrylates.

The process according to the invention is suitable for isolating and/or purifying nucleic acids of various origins, for example from cells, tissue materials, blood or pathogens. Before isolating the nucleic acids, the material to be investigated is disrupted by techniques known per se, such as, for example, disruption by protease digestion, resulting in a sample suitable for subsequent steps A to C, a lysate. Where appropriate, the biological material is lysed in a step inserted after process step A). Other suitable disruption methods have been described in DE-A-4 333 805.

The sample is mixed with the bead polymer according to the invention at a pH of 7 or below, preferably in the range from 2 to 6, particularly preferably in the range from 2 to 3, at room temperature. The bead polymer is removed with the aid of a magnetic field. The complex of nucleic acid and bead polymer obtained in this way can then be purified by washing with suitable buffers.

To liberate the bound nucleic acids from the complex, the pH of the complex is then adjusted to pH values above 7, preferably from 8 to 14, particularly preferably in the range 12 to 14.

The bead polymers according to the invention provide higher adsorption and release rates than the soluble polymers disclosed in EP-A-0 707 077. Isolation can be carried out more easily, that is to say with fewer steps and in shorter times. The purity of the isolated nucleic acids is higher and, in particular, they contain fewer inhibiting by-products, so that amplification of the nucleic acids, for example, the so-called "PCR" and the "RT-PCR" takes place particularly well. The process according to the invention is also superior to the method described in EP-A-0 707 077 in relation to restriction enzyme digestion of the nucleic acids obtained.

The bead polymers according to the invention are also very suitable for amplifying the adsorbed nucleic acids for example by the so-called "Taqman PCR" directly on the bead polymers (that is to say without step C).

EXAMPLE 1

Preparation of a Bead Polymer According to the Invention

1a) Preparation of a Dispersing Aid

A solution of 1324 g of cyclohexane, 511 g of methacrylic acid $C_{13}$-ester, 57 g of hydroxyethyl methacrylate and 3.8 g of dibenzoyl peroxide in a 41 reaction vessel with gate stirrer, gas inlet tube and gas outlet tube was heated under a nitrogen atmosphere at 300 rpm to 78° C. over the course of 2 h, kept at this temperature for 10 h, then heated to 90° C. and kept at this temperature for a further 1.5 h. It was then cooled to 25° C. 1835 g of a 30.5% by weight solution of a dispersant were obtained. The Staudinger index, measured using an Ubbelohde viscometer at 25° C., was 72.6 ml/g.

1b) Preparation of a Crosslinked Bead Polymer 41.25 g of dispersant solution from 1a) and 240 g of cyclohexane were introduced into a 0.5 liter reaction vessel with gate stirrer, reflux condenser and thermosensor and were stirred. 9.38 g of N,N.-dimethylaminoethyl methacrylate were stirred with 13.3 g of water and 5.89 g of 37% strength hydrochloric acid for 5 minutes and neutralized with 0.6 g of 1N NaOH. This solution was then added to the reaction vessel. To this mixture were added 20.31 g of acrylamide and 1.56 g of methylene-N,N'-bisacrylamide, dissolved in 8 g of methanol. 0.063 g of potassium peroxodisulphate dissolved in a mixture of 4.25 g of water and 2 g of methanol was added to this reaction mixture, which was then flushed with nitrogen gas at 450 rpm for 10 minutes. The stirring speed was then raised to 1 000 rpm and the temperature was increased to 60° C. over the course of 1 hour, and the temperature was kept at this for 10 hours. After cooling, the resulting polymer was removed from the reaction solution by decantation and purified three times each with cyclohexane, water and methanol, and dried in a vacuum oven at 40° C. 14.7 g of dried bead polymer with an average particle size of 12 μm and a swelling index of 6 at 25° C. in water were obtained.

1c) Doping of the Bead Polymer With Iron Oxide

In a stirred vessel with a magnetic stirrer and thermometer, 3.625 g of iron(II) chloride tetrahydrate, 1.5 g of iron(III) chloride (anhydrous) and 0.3 g of sodium bisulphite were dissolved in 5.75 ml of water.

5 g of dry bead polymer (1b) were introduced into a 100 ml three-neck flask and cooled externally with ice, and then the iron salt solution described above was added. The resulting suspension was stirred for 35 minutes and then heated externally with boiling water until the suspension had become a solid mixture. The bead polymer was then stirred in another 500 ml flask with an alkaline solution of 67.5 ml of water and 8.5 ml of 26% strength ammonia solution (pH=9) for 1 hours and diluted with 250 ml of water. After decantation of this solution, this procedure was repeated several times.

The bead polymer treated with iron salt solution was mixed with 300 ml of water and stirred under a stream of air for 30 minutes and then heated to 72° C. The pH was set at 9 throughout the procedure by adding ammonia solution. 0.155 g of potassium peroxodisulphate was then added to the solution, which was heated at 72° C. for a further 2.5 hours. After the liquid had been decanted off, the solid was washed five times with water, treating with ultrasound. 5.1 g of black bead polymer with an iron content of 6% by weight, which was strongly attracted by an inhomogeneous magnetic field, were obtained.

EXAMPLE 2

Preparation of a Bead Polymer According to the Invention

2a) Preparation of a Crosslinked Bead Polymer 41 g of dispersing aid solution from 1a) and 240 g of cyclohexane were introduced into a 0.5 liter reaction vessel with gate stirrer, reflux condenser and thermosensor and were stirred. 9.38 g of N,N-dimethylaminoethyl methacrylate were stirred with 13.3 g of water and 6 g of 37% strength hydrochloric acid for 5 minutes. This solution was then added to the reaction vessel. To this mixture were added 18.75 g of acrylamide and 3.13 g of methylene-N,N'-bisacrylamide, dissolved in 8 g of methanol. 0.313 g of 2,2'-azobis(2-amidinopropane) dihydrochloride dissolved in a mixture of 4.25 g of water and 2 g of methanol was added to this reaction mixture, which was then flushed with nitrogen gas at 450 rpm for 10 minutes. The temperature was then increased to 60° C. over the course of 1 hour at 800 rpm, and reaction was allowed to take place at this temperature for 10 hours. After cooling, the resulting polymer was removed from the reaction solution by decantation and purified three times each with cyclohexane, water and methanol, and dried in a vacuum oven at 40° C. 15 g of dried bead polymer with an average particle size of 20 μm and a swelling index of 5 at 25° C. in water were obtained.

2b) Doping of the Bead Polymer With Iron Oxide 5 g of the bead polymer from 2a) were doped with iron oxide as described under 1c). The entire procedure was carried out twice in this case. 5.4 g of black bead polymer with an iron content of 8.3% by weight, which is strongly attracted by an inhomogeneous magnetic field, were obtained.

What is claimed is:

1. Crosslinked bead polymers doped with superparamagnetic iron oxide and containing basic amino groups, wherein the bead polymers comprise copolymerized units of hydrophilic (meth)acrylate and amino (meth)acrylates.

2. Crosslinked bead polymers according to claim 1, wherein the hydrophilic (meth)acrylate is (meth)acrylamide.

3. Crosslinked bead polymers according to claim 1, wherein the amino (meth)acrylate is an aminoalkyl methacrylate.

4. Crosslinked bead polymers according to claim 3, wherein the bead polymers comprise copolymerized units of (meth)acrylamide and dialkylaminoalkyl (meth)acrylates and wherein methylenebis(meth)acrylamide comprises a crosslinker.

5. Crosslinked bead polymers according to claim 1, having a particle size of from 5 to 100 μm.

6. Crosslinked bead polymers according to claim 5, wherein the particle distribution $D_v/D_z$ is less than 2.5.

* * * * *